United States Patent
Renaud

(10) Patent No.: US 8,258,364 B2
(45) Date of Patent: Sep. 4, 2012

(54) METHOD FOR STEAM BIOMASS REACTOR

(76) Inventor: Regis P. Renaud, Silverado, CA (US)

( * ) Notice: Subject to any disclaimer, the term of this patent is extended or adjusted under 35 U.S.C. 154(b) by 630 days.

(21) Appl. No.: 12/485,829

(22) Filed: Jun. 16, 2009

(65) Prior Publication Data

US 2009/0314625 A1    Dec. 24, 2009

Related U.S. Application Data

(60) Provisional application No. 61/061,991, filed on Jun. 16, 2008, provisional application No. 61/073,709, filed on Jun. 18, 2008.

(51) Int. Cl.
*A62D 3/32* (2007.01)
(52) U.S. Cl. ........................................ 588/314; 588/405
(58) Field of Classification Search ................ 588/312, 588/314, 317, 405
See application file for complete search history.

(56) References Cited

U.S. PATENT DOCUMENTS

| | | | |
|---|---|---|---|
| 3,550,791 A | 12/1970 | Smith et al. |
| 3,586,624 A | 6/1971 | Larson |
| 3,747,516 A | 7/1973 | Wood |
| 3,859,404 A | 1/1975 | Immel et al. |
| 3,891,738 A | 6/1975 | Shen |
| 3,941,528 A | 3/1976 | Cotterell |
| 4,100,023 A | 7/1978 | McDonald |
| 4,119,741 A | 10/1978 | Stahler |
| 4,141,694 A | 2/1979 | Camacho |
| 4,142,912 A | 3/1979 | Young |
| 4,149,870 A | 4/1979 | Kozuki |
| 4,153,514 A | 5/1979 | Garrett et al. |
| 4,181,504 A | 1/1980 | Camacho |
| 4,252,901 A | 2/1981 | Fischer et al. |
| 4,323,367 A | 4/1982 | Ghosh |
| 4,334,997 A | 6/1982 | Peterson |
| 4,369,597 A | 1/1983 | Leep et al. |
| 4,377,066 A | 3/1983 | Dickinson |
| 4,448,589 A | 5/1984 | Fan et al. |
| 4,469,176 A | 9/1984 | Zison et al. |
| 4,473,590 A | 9/1984 | Weigandt et al. |
| 4,481,293 A | 11/1984 | Thomsen et al. |
| 4,518,399 A | 5/1985 | Croskell et al. |
| 4,523,928 A | 6/1985 | Hillman et al. |
| 4,540,495 A | 9/1985 | Holloway |
| 4,557,826 A | 12/1985 | Flucher et al. |
| 4,649,741 A | 3/1987 | Strom |
| 4,670,148 A | 6/1987 | Schneider |
| 4,684,468 A | 8/1987 | De Baere |
| 4,731,179 A | 3/1988 | De Baere |
| 4,788,936 A | 12/1988 | Billings |
| 4,798,801 A | 1/1989 | Hitzman |
| 4,844,351 A | 7/1989 | Holloway |
| 4,845,034 A | 7/1989 | Menger et al. |
| 4,892,647 A | 1/1990 | Liddle et al. |
| 4,926,586 A | 5/1990 | Nagamatsu |
| 4,936,996 A | 6/1990 | Messing |
| 5,009,697 A | 4/1991 | Martin et al. |
| 5,021,077 A | 6/1991 | Moore |
| 5,061,735 A | 10/1991 | Zielinski |
| 5,075,057 A | 12/1991 | Hoedl |
| 5,139,365 A | 8/1992 | Chesner |
| 5,144,940 A | 9/1992 | Fiarkoski, Sr. |
| 5,190,088 A | 3/1993 | Thomassen et al. |
| 5,238,580 A | 8/1993 | Singhvi |
| 5,240,656 A | 8/1993 | Scheeres |
| 5,254,465 A | 10/1993 | Wise |
| 5,261,766 A | 11/1993 | Anderson |
| 5,264,349 A | 11/1993 | De Baere |
| 5,265,979 A | 11/1993 | Hansen |
| 5,280,757 A | 1/1994 | Carter et al. |
| 5,318,909 A | 6/1994 | De Baere |
| 5,362,181 A | 11/1994 | DenBesten |
| 5,389,258 A | 2/1995 | Smis et al. |
| 5,411,697 A | 5/1995 | McGraw et al. |
| 5,447,850 A | 9/1995 | McCann |
| 5,472,997 A | 12/1995 | Koslowski et al. |
| 5,484,231 A | 1/1996 | Cannan et al. |
| 5,494,626 A | 2/1996 | Middleton |
| 5,494,627 A | 2/1996 | Kargol et al. |
| 5,507,396 A | 4/1996 | Hauch |
| 5,510,030 A | 4/1996 | Bacher et al. |
| 5,564,862 A | 10/1996 | Markels, Jr. |
| 5,587,320 A | 12/1996 | Shindo et al. |

(Continued)

FOREIGN PATENT DOCUMENTS

JP    409279161 A    10/1997

(Continued)

OTHER PUBLICATIONS www.statigraphics.com/services.html, 8 pages, "Penetrometer soil exploration system", undated, prior to 2003.

(Continued)

*Primary Examiner* — Edward Johnson
(74) *Attorney, Agent, or Firm* — Knobbe Martens Olson & Bear LLP

(57) ABSTRACT

A method and apparatus for a steam biomass reactor converts organic waste placed inside a sealed steam injected reactor to biogas (methane $CH_4$ and carbon dioxide $CO_2$). The amount of liquid introduced into the reactor can be minimized, increased methane and $CO_2$ can be produced, and the methane produced can have higher Btu values as compared to methane produced in other reactors. Some embodiments provide a method of injecting steam into a sealed vessel that is loaded with organic waste and collecting the methane produced by accelerated decomposition/biodegradation of the organic component of the waste within the vessel. The steam accelerates the decomposition of the organic refuse, thereby enhancing the production of methane gas and $CO_2$.

18 Claims, 3 Drawing Sheets

U.S. PATENT DOCUMENTS

| | | |
|---|---|---|
| 5,605,417 A | 2/1997 | Englert et al. |
| 5,634,414 A | 6/1997 | Camacho |
| 5,649,785 A | 7/1997 | Djerf et al. |
| 5,660,282 A | 8/1997 | Djerf et al. |
| 5,695,641 A | 12/1997 | Cosulich et al. |
| 5,727,455 A | 3/1998 | Yerman |
| RE35,782 E | 5/1998 | Circeo, Jr. et al. |
| 5,770,784 A | 6/1998 | Heywood et al. |
| 5,795,479 A | 8/1998 | Vogt et al. |
| 5,802,763 A | 9/1998 | Milstein |
| 5,824,246 A | 10/1998 | Reetz |
| 5,860,907 A | 1/1999 | Kauschinger |
| 5,908,267 A | 6/1999 | Schuring et al. |
| 5,911,195 A | 6/1999 | Tripp et al. |
| 5,964,985 A | 10/1999 | Wootten |
| 5,976,435 A | 11/1999 | Djerf et al. |
| 5,984,580 A | 11/1999 | Ham et al. |
| 6,012,517 A | 1/2000 | Schuring et al. |
| 6,013,158 A | 1/2000 | Wootten |
| 6,017,475 A | 1/2000 | Cantrell |
| 6,024,513 A | 2/2000 | Hudgins et al. |
| 6,036,971 A | 3/2000 | Kimoto et al. |
| 6,050,423 A | 4/2000 | Dunnuck et al. |
| 6,077,494 A | 6/2000 | Gasiorowski et al. |
| 6,106,197 A | 8/2000 | Kozak et al. |
| 6,149,012 A | 11/2000 | Brooks et al. |
| 6,182,610 B1 | 2/2001 | Tripp et al. |
| 6,200,475 B1 | 3/2001 | Chen |
| 6,299,774 B1 | 10/2001 | Ainsworth et al. |
| 6,313,194 B1 | 11/2001 | Yagi et al. |
| 6,344,165 B1 | 2/2002 | Coleman |
| 6,348,174 B1 | 2/2002 | Hall |
| 6,458,747 B1 | 10/2002 | Kulik |
| 6,471,443 B1 | 10/2002 | Renaud |
| 6,605,245 B1 | 8/2003 | Dubelsten et al. |
| 6,623,676 B1 | 9/2003 | Davis et al. |
| 6,824,686 B2 | 11/2004 | Smis et al. |
| 6,905,601 B2 | 6/2005 | De Baere et al. |
| 7,018,582 B2 | 3/2006 | Lewis |
| 7,028,478 B2 | 4/2006 | Prentice, III |
| 7,067,164 B2 | 6/2006 | Yamamoto |
| 7,314,190 B2 | 1/2008 | Palm |
| 7,347,391 B2 | 3/2008 | Michalek et al. |
| 7,452,392 B2 | 11/2008 | Nick et al. |
| 2001/0024727 A1 | 9/2001 | Dubelsten et al. |
| 2002/0125600 A1 | 9/2002 | Horne |
| 2002/0179493 A1 | 12/2002 | Etter |
| 2003/0157297 A1 | 8/2003 | Lewis |
| 2004/0250700 A1 | 12/2004 | Renaud |
| 2005/0120715 A1 | 6/2005 | Labrador |
| 2006/0032788 A1 | 2/2006 | Etter |
| 2006/0053791 A1 | 3/2006 | Prentice, III |
| 2006/0112639 A1 | 6/2006 | Nick et al. |
| 2006/0225422 A1 | 10/2006 | Prentice, III |
| 2007/0144027 A1 | 6/2007 | Renaud |
| 2007/0180955 A1 | 8/2007 | Warner |
| 2007/0251433 A1 | 11/2007 | Rabiner |
| 2008/0138885 A1 | 6/2008 | De Baere et al. |
| 2008/0147241 A1 | 6/2008 | Tsangaris et al. |
| 2008/0155985 A1 | 7/2008 | Labrador |
| 2008/0209807 A1 | 9/2008 | Tsangaris et al. |
| 2009/0039184 A1 | 2/2009 | Vanderpool |
| 2009/0041639 A1 | 2/2009 | Vanderpool |

FOREIGN PATENT DOCUMENTS

| | | |
|---|---|---|
| WO | WO 2006/015423 | 2/2006 |

OTHER PUBLICATIONS

ConeTec Brochures, "The Electrical Resistivity Cone" and "The Piezo Cone Penetrometer", 3 pages, undated, prior to 2003.

www.cerf.org/research.clusters/4-3.htm, "Non Invasive Characterization of Site Conditions", 3 pages, © 1997.

www4.ivenue.com/landfillengineering.com/ "Landfill Engineering", Steam Injection in Landfills, 16 pages total, prior to 2003.

Brecht II Dranco—Anaerobic Digestion Facility (Belgium), in 9 pages, Oct. 18, 2004.

International Search Report and Written Opinion of the International Searching Authority for PCT Application No. PCT/US2009/035570, date of mailing Sep. 30, 2009.

METHOD FOR STEAM BIOMASS REACTOR

CROSS-REFERENCE TO RELATED APPLICATIONS

This application claims the benefit under 35 U.S.C. §119 (e) of U.S. Provisional Application No. 61/061,991, filed Jun. 16, 2008 and U.S. Provisional Application No. 61/073,709, filed Jun. 18, 2008, the entire contents of all of which are hereby incorporated by reference herein and made a part of this specification. U.S. application Ser. No. 12/395,192, filed Feb. 27, 2009 is also incorporated by reference herein and made a part of this specification.

BACKGROUND OF THE INVENTION

1. Field of the Invention

Some embodiments of the present invention relate to methods of treating animal waste, green waste, paper/cardboard waste and other organic waste.

2. Description of the Related Art

Millions of tons of cow, chicken, pig and horse manure are produced every day in the United States. Millions of tons of other organic waste are also produced everyday that is not taken to municipal solid waste landfills. The disposal of waste is a major problem for farmers and other waste producers.

One way in which waste producers dispose of waste is to convert it into biogas. Currently, a 9:1 mix of water to manure is used in water based bioreactors requiring 14,400,000 gallons of water to convert 6,000 tons of manure into biogas. However, this process not only uses a tremendous amount of water, but also it does not decompose all of the manure or waste. Usually this residue called repeat is used as a soil amendment. These wet reactors produce thousands of gallons of water saturated with biogas, which then must be extracted from the water. This lengthy process usually takes about 21 days before any biogas can be recovered.

SUMMARY OF THE INVENTION

This disclosure advantageously provides an alternative to current approaches and produces significantly more methane gas with little or no waste water. Some embodiments convert most all of the organic waste placed inside the sealed steam injected reactor and produce biogas (including methane $CH_4$ and carbon dioxide $CO_2$). Often, the only residue that remains in the steam reactor will be the dirt and debris picked up with the waste along the way to the reactor.

A method of injecting steam into a sealed vessel has several features, no single one of which is solely responsible for its desirable attributes. Without limiting the scope of these inventions, some of the more prominent features will now be discussed briefly. After considering this discussion, and particularly after reading the section entitled "Detailed Description," one will understand how the features of these inventions provide advantages, which can include, for example: minimization of the amount of liquid introduced into the reactor, total moisturization, increased methane and $CO_2$ production, and production of methane having higher Btu values as compared to methane produced in other reactors.

Whereas wet reactors in use today operate in the aqueous phase, the methods and apparatus disclosed herein can operate in the vapor to bio-film phase. Steam expands 1,600 times its original volume. Therefore, much less water can be required to biodegrade the organic waste with steam and produce a maximum amount of biogas with little to no wastewater. Moisture and heat accelerates decomposition of organic refuse. Pilot Study data from steam injection in landfills indicates that 1 volume of steam can create 1 equal volume of landfill gas or biogas.

Some embodiments provide a method of injecting steam into a sealed vessel that is loaded with organic waste and collecting the methane produced by accelerated decomposition/biodegradation of the organic component of the waste within the vessel. The steam accelerates the decomposition of the organic refuse, thereby enhancing the production of methane gas and $CO_2$. Anaerobic digestion processes contribute to the production of this gas. Once the organic waste is inoculated with bacteria, biogas recovery can begin within hours instead of the 21 days required by many typical current systems that employ wet processes.

The reduced decomposition time can allow for a continuous flow of organic waste into the reactor. It has been found that according to certain methods, for every approximately 12,000 cubic feet of biogas produced, approximately 1 ton of organic waste has been converted to gas. In addition, for every approximately 12,000 cubic feet of steam injected, approximately 12,000 cubic feet of biogas is produced, with at least approximately 50% to approximately 60% methane and approximately 40% to approximately 50% $CO_2$. Therefore, every approximately 56 gallons of water converted to steam can produce approximately 12,000 cubic feet of biogas and remove approximately 1 ton of organic waste from the reactor. Any excess moisture in the organic waste itself can exit the reactor with the biogas as most biogas is usually saturated with a moisture content of approximately 2 to 12% water vapor.

Some embodiments provide a method of enhancing the digestion of organic material including the steps of placing organic material into a substantially air-tight vessel, enriching steam with a chemical configured to precipitate H2S, and injecting the enriched steam into the organic material. Some embodiments further provide for the collection of biogas produced during the enhanced digestion of the organic material. Some embodiments further provide for driving a steam producing apparatus with a least a portion of the collected biogas, wherein the steam is injected into the substantially air-tight vessel.

Some embodiments provide a method of producing biogas from waste material including the steps of conveying a waste material from a first container to a second substantially air-tight container, injecting steam into the waste material in the second container, extracting biogas from the waste material in the second container with a gas extractor, monitoring a height level of the waste material in the second container, and controlling the amount of waste material conveyed from the first container into the second container such that as the waste material is converted into biogas, the gas extractor is maintained under the top level of waste material in the second container.

Some embodiments provide an apparatus for producing biogas from waste material comprising a substantially air-tight vessel configured to facilitate the processing of the waste material into biogas, a hopper configured to be filled with waste material, a first conveyer to convey the waste material from the hopper to the vessel, a steam-line for injecting steam into the vessel, and a gas extractor for extracting biogas from the vessel.

Some embodiments provide a method for the extraction of biogas from organic material. Organic material is placed into a first container. The material is purged of air. The material is then conveyed into a substantially air-tight second container. Steam is injected into the second container to facilitate the decomposition of the organic material and the generation of biogas. Biogas is extracted from the second container. Additional organic material is added to the second container, either continuously or as needed, to maintain a desired level of material in the second container. The level of material can be monitored such that the supply of additional material is controlled. The substantially air-tight condition of the second container can be maintained by providing a seal between the first container and the second container. In some embodiments, the seal is maintained by keeping a continuous feed of material in the conveyer system between the first and second containers. In some embodiments, the conveyer system is a screw auger. As the level of material in the second container approaches or drops below a desired threshold, additional material can be fed into the container. In some embodiments, the level of material is monitored in one or both containers with a light and camera system. The migration of steam through the material in the second container can be controlled to achieve a desired level of biogas production. In some embodiments, densifying the material in the second container, for example by incorporating smaller particulate or by assisting in the settling of the material, can slow the migration of steam through the material. In some embodiments, barriers can be used over the biogas extractors to reduce the amount of moisture drawn out of the second container.

BRIEF DESCRIPTION OF THE DRAWINGS

Some embodiments will now be discussed in greater detail. These embodiments depict the novel and non-obvious method and associated apparatus for injecting steam into a reactor shown in the accompanying drawings, which are for illustrative purposes only. These drawings include the following figures, in which like numerals indicate like parts.

DETAILED DESCRIPTION

Figure 1:
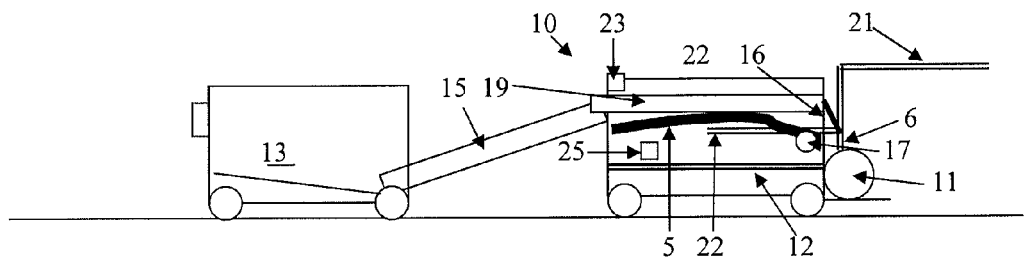
FIG. 1 is a schematic side view of an apparatus for performing some embodiments of the present method.

In some embodiments, steam can be injected into a biomass reactor tank 10. This can allow the reactor 10 to operate in the vapor to bio-film phase. The steam can promote the anaerobic biodegradation of the organic refuse in the reactor 10, which in turn increases methane gas generation.

The size of the steam biomass reactor can be of any size, including but not limited to: tank truck or trailers mounted on wheels to very large silos to thousands of cubic foot sealable tanks. The reactor used to convert the waste to biogas is preferably a substantially air-tight vessel to maintain anaerobic conditions. To provide a controlled continuous flow of waste into the reactor, and to maintain anaerobic conditions, another sealed vessel can be used as a hopper to be preloaded with waste which can be purged with inert gas or $CO_2$ in steam, and conveyed to the reactor by, for example, a screw auger system. The purging process preferably removes air from the waste to allow the methanogens to flourish in the reactor, increasing the biogas production. Each time the hopper is opened to add more waste, it is possible the hopper will become contaminated with air. In some embodiments, the substantially air-tight seal on the reactor can be maintained despite the contamination during the hopper refill by keeping a continuous stream of waste in the auger system between the storage hopper and the reactor. Thus, when the hopper is opened to add additional waste, waste in the auger keeps the air trapped in the hopper until it can be purged.

The steam can be derived from, but not limited to, a source such as a boiler, heat exchanger, solar panels, geothermal, or power plant waste heat.

Some embodiments of the invention can include one or more of the following components:

One or more sealed vessel(s) that can generally be airtight and can hold a volume of organic waste.

The sealed vessel(s) can be one or more horizontal or vertical tanks.

One or more perforated steam line(s) at or near various portions of the vessel including the top, the bottom, or one end.

One or more temperature and/or moisture sensors can be installed at various locations on or in the vessel to monitor steam migration within the vessel and the waste.

One or more boiler(s) or other devices to make steam.

One or more water supply, for example a water tank or water line to supply the boiler(s).

One or more sealable hopper tank(s) with a system for conveying the waste to the reactor, for example a screw auger system.

One or more batch tank(s) or storage hoppers to allow de-airing of the waste prior to starting the bioreaction one batch at a time instead of continual feeding of the reactor.

One or more waste spreader device(s) inside the reactor to evenly distribute the waste inside the reactor for a continuous feed.

One or more hopper-purge system(s) to remove the oxygen from the loading process.

One or more hydrophobic filter(s) can be placed before the gas extraction pipe from the reactor.

The biogas can be sent to a gas scrubber via pipeline or other mechanism to remove the $CO_2$ portion of the biogas or it can be used in its raw form.

One or more removal system(s), for example a screw auger, can be used to remove indigestible material from the reactor. The indigestible material can be located at the bottom of the reactor and the removal system(s) can be configured to remove the material from the bottom. In some embodiments, some of this waste debris can be conveyed to the hopper tank(s) and used as inoculate for the fresh waste being purged prior to entering the reactor tank. This can be done with, for example, an additional auger or augers.

If hydrogen sulfide ($H_2S$) gas is generated during the bioprocess, ferric chloride may be added to the water, for example, prior to it entering the boiler or directly into the steam stream and injected into the bioreactor tank. This can precipitate the $H_2S$ from the biogas prior to it being extracted from the bioreactor tank. Though ferric chloride is preferred, other chemicals may be employed to precipitate the $H_2S$ from the biogas.

One or more pressure relief valve(s) can be used to prevent gas overpressure.

A light and camera system can be used inside the hopper tank to monitor the discharge from the hopper tank and/or another light and camera system can be inside the reactor tank to monitor the settlement of the waste pile as it biodegrades.

FIG. 1 schematically illustrates an apparatus for performing some embodiments of the present method. This smaller unit can be portable and could be used on smaller farms/dairies for lower tonnage per day. The hopper 13 can be filled from the top, sealed, and purged with various gases and/or steam, including inert gas. The purged waste can then be conveyed 15 to the reactor 10 by way of a conveyer 15, for example a screw auger. Though screw auger systems are preferred, other conveyance methods are also possible. It is particularly advantageous that the conveyance method maintain a seal in the reactor 10 as the waste is conveyed into the reactor 10 for maximum biogas production. A spreader 19, for example a screw auger, can be positioned on the upper portion of the reactor 10 and can distribute the waste across the full length of the reactor 10. A boiler 11 is shown at the end of the reactor 10 which is fired by, for example, using some of the biogas from the reactor, through pipeline 6, to make steam. A steam line/injector 12 from the boiler 11 may be placed at the bottom or at one end of the reactor 10. The boiler 10 could be, for example, a heat exchanger, solar panel system, waste heat from a power plant or a geothermal system.

Figure 2:
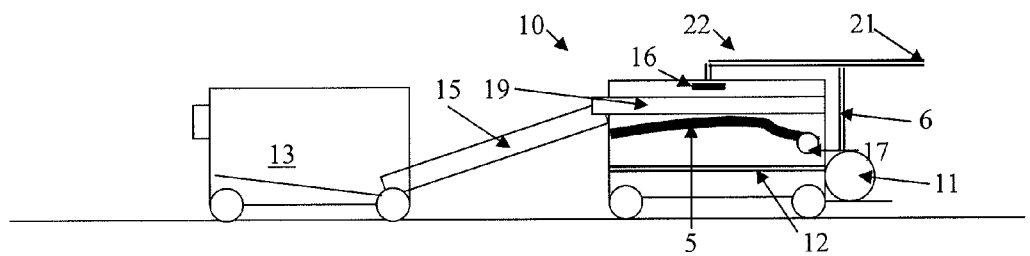
FIG. 2 is a schematic side view of another apparatus for performing some embodiments of the present method.
Figure 3:
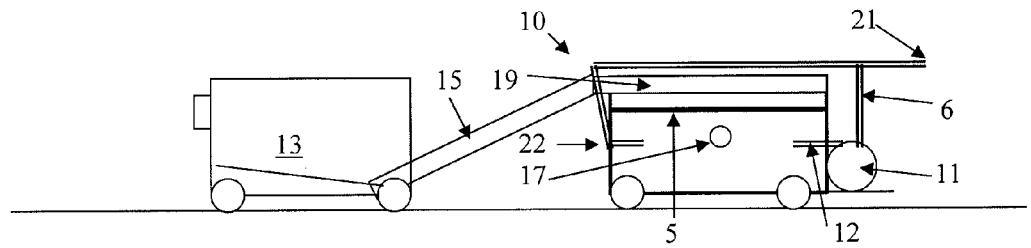
FIG. 3 is a schematic side view of another apparatus for performing some embodiments of the present method.

FIGS. 1-3 illustrate various exemplary configurations for the biomass reactor system. In some embodiments, the methane and $CO_2$ can be collected through a pipeline 21 at or near the top of the reactor 10 (FIG. 2) or at the opposite end of the reactor 10 from the steam injector 12 (FIG. 3). A gas extractor 22 may be installed at or near the top or at the opposite end of the reactor from the steam injector 12. It is preferred that the gas extractor 22 is installed and maintained under the top level of the waste prism 5 to prevent steam from short-circuiting and being extracted before it has a chance to convert the waste to biogas (FIG. 1). A hydrophobic filter 16 can be placed at the inlet of the extraction gas pipeline 22 to remove moisture from the bio-gas. A gas line 21 can take the gas from the gas extractor 22 to a scrubber (not shown) or to other locations, for example, for storage or use.

Steam pipelines 12 can be positioned within the reactor 10. The arrangement depicted in FIG. 1 is merely exemplary. The location for the steam lines 12 can be determined during the design of the apparatus, and may differ significantly from the arrangement of FIG. 1 as demanded by a particular application. Some embodiments of a steam biomass reactor 10 include injecting steam at or near the bottom of a layer of organic waste inside an airtight vessel at such a rate as to allow the steam to convert a portion of the waste into biogas. If the steam is injected too fast, it can blow through the waste cell or prism and limit the conversion.

In some embodiments, the steam injector 12 may be placed at or near the mid-level of one end of the vessel. At the opposing end of the vessel, the gas extraction pipe 22 can also be placed at or near the mid-level of the vessel. The waste is then filled to the desired depth in the vessel. The steam is then injected at one end and by the time the steam is drawn through the organic waste, it should be converted to biogas and extracted out of the other end of the vessel. This embodiment should reduce the possibility of steam by-passing the organic mass before it is converted to biogas and extracted.

The speed of the steam migration through the waste can be controlled to increase or decrease the biogas production. One method of controlling the steam migration is to control the size of the organic waste particulate in the waste prism. In some embodiments, a particle size of approximately ½ inch is preferred to limit the amount of steam that moves through the waste too fast, thereby being extracted before it is converted by the methanogens to biogas.

Sensors 17 can be installed at various locations around the tank to monitor various aspects inside the reactor 10, including sensors to monitor the migration of the steam and the temperature of the waste/feedstock. A relief valve 23 may also be installed to prevent over pressurizing the reactor tank.

Temperature sensors 17 may monitor the amount of steam migrating through the waste mass so that the conversion can be better controlled. If the temperature of the top of the waste mass becomes too high, this can indicate that the waste pile is too short and/or that the steam may be passing through the waste before it is being converted to biogas. In some embodiments, more organic waste can be placed on top of the waste mass, thereby cooling the steam and forcing it to slow down and convert more of the mass.

Temperature and moisture sensors 17 are preferably distributed throughout the vessel to monitor the conditions within the waste column. Feedback from these sensors enables the amount of steam injection to be adjusted to prevent steam from blowing through the waste before it is converted to biogas.

Shakers 25 are preferably used to settle and densify the waste to slow down the migration of the steam through the waste prism as it biodegrades. Electric, pneumatic, or hydraulic shakers/vibrators 25 can be placed at various locations around the outside reactor tank wall.

The source of steam 11 may be a gas-fired boiler or from waste heat of another source. The steam injected into the reactor 10 raises the moisture content and the heat of the organic waste. Moisture and heat promotes the rapid decomposition of the organic waste, while at the same time raising the amount of methane gas produced during decomposition. It is important to maintain the proper temperature of the bioreactor. Methanogens prefer to live in temperatures ranging from approximately 80° F. to 140° F. Sulfur reducing bacteria that produce $H_2S$ prefer to live in temperatures ranging from approximately 150° F. to 190° F. The rapid decomposition of the organic refuse causes the rapid settling of the waste pile in the reactor, enabling, in some embodiments, a continuous feed of waste.

Injecting steam into the reactor 10 can be more advantageous than injecting water for a variety of reasons. For example, water expands to approximately 1,600 times its original volume upon boiling. Thus, injecting steam allows total coverage of the organic waste using only a small fraction of the water that would otherwise be needed. Using less water minimizes other environmental issues and saves costs.

Another advantage is that steam, which is a vapor, moves through the waste as much as 1,000 times faster than water, and therefore can convert the waste to biogas much faster. It is recognized in the anaerobic digester industry that soft tissue waste will convert to biogas faster than hard or dense material such as woody tissue. However, in a vertical reactor 10 the denser material will move down inside the waste pile as the soft tissue biodegrades bringing the denser material closer to the steam injection ports 12. As the steam breaks down the denser material it will allow the methanogens to digest this material. This material can also be re-injected into the hopper tank 13 via another auger system 20 as inoculate for fresh waste being conveyed to the reactor tank allowing more time for this dense material to convert to biogas.

Some embodiments of a steam reactor will use approximately 337,000 gallons of water to biodegrade the amount of organic waste it normally takes approximately 14,400,000 gallons of water to biodegrade. In addition, the denser material is usually removed from a wet digester after 21 days and disposed of, whereas denser material can be digested in some embodiments of a steam reactor, as explained above.

To achieve these and other advantages, in some embodiments the method of conveying the organic waste into the reactor 10 includes first placing waste into a sealable hopper 13 and then purging the waste with inert gas. The waste can then be conveyed to the reactor via a screw auger 15 or similar conveyance. The waste is then spread evenly over the waste bed by another screw auger or a rotary spreader 19. The purging process preferably removes air from the waste to allow the methanogens to flourish in the reactor 10, increasing the biogas production. Each time the hopper 13 is opened to add more waste, it is possible the hopper 13 will become contaminated with air. In some embodiments, the seal on the reactor 10 can be maintained despite the contamination during the hopper refill by keeping a continuous stream of waste in the auger system 15 between the storage hopper 13 and the reactor 10. Thus, when the hopper 13 is opened to add additional waste, waste in the auger 15 keeps the air trapped in the hopper 13 until it can be purged.

In some embodiments, the biogas can be filtered with a hydrophobic membrane 16 prior to being extracted from the reactor 10.

Figure 4:
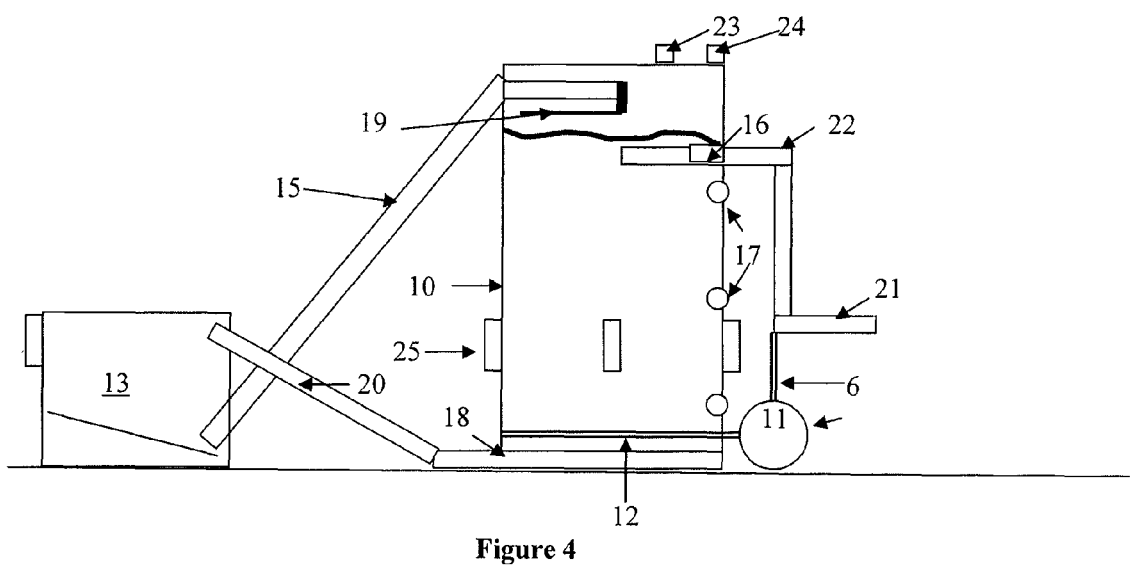
FIG. 4 is a schematic side view of an apparatus with a larger reactor unit.

FIG. 4 is a schematic side view of the apparatus of a larger reactor unit. The reactor tank can be of any size. A rotary spreader 19 could be used for, but not limited to, spreading the waste evenly over the organic waste bed. The hopper 13 may be filled from the top, sealed, and purged with inert gas and/or steam and then the waste can be conveyed, by for example a screw auger 15 or other conveyor, to the reactor 10. A boiler 11 which is fired by, for example, using some of the biogas from the reactor 10 or other fuels, can be used to make steam. Steam can also be produced by other means such as, for example, heat exchangers, solar collectors, geothermal, or waste heat. A steam line/injector 12 from the boiler 11 may be placed at the bottom or top of the reactor 10.

A gas extractor 22 may be installed at the top or at the opposite end of the reactor 10 from the steam injector 12. In some embodiments, it is preferred that the gas extractor 22 is installed and maintained under the top level of the waste prism to limit the amount of steam that can short-circuit the waste prism and be extracted before it has a chance to convert the biogas. In addition, a hydrophobic filter 16 can be placed at the inlet of the extraction gas pipeline 22 to remove moisture from the biogas.

In the embodiment illustrated in FIG. 4, sensors 17 are installed at various locations around the tank to monitor the migration of the steam and the temperature of the waste/feedstock. A relief valve 23 may be installed to prevent over pressurizing the reactor tank 10.

A light and camera system 24 could be used to monitor the discharge of the hopper tank 13 and/or the settlement of waste pile as it biodegrades in the reactor tank 10. White paint lines or other lines of a preferably contrasting color with the inside of the tank, can be marked on the inside wall of the tank at equal intervals. This can be used with the light and camera system 24 to observe the downward movement of the waste from the hopper 13 or the waste pile in the reactor tank 10 as it biodegrades and the upward level of waste as the reactor tank 10 is refilled. Shakers 25 placed around the reactor tank 10 may be used to settle and densify the waste to slow down the migration of the steam through the waste pile.

Over time, inorganic residue (for example, soil) may build up at the bottom of the reactor 10. One or more removal system(s) 18, for example a screw auger or similar conveyance, can be used to remove this material from the reactor 10. This material can be located at the bottom of the reactor 10 and the removal system(s) 18 can be configured to remove the material from the bottom. In some embodiments, some of this waste debris can be conveyed to the hopper tank(s) 13 and used as inoculate for the fresh waste being purged prior to entering the reactor tank 10. This can be done with, for example, an additional auger or augers 20.

Figure 5:
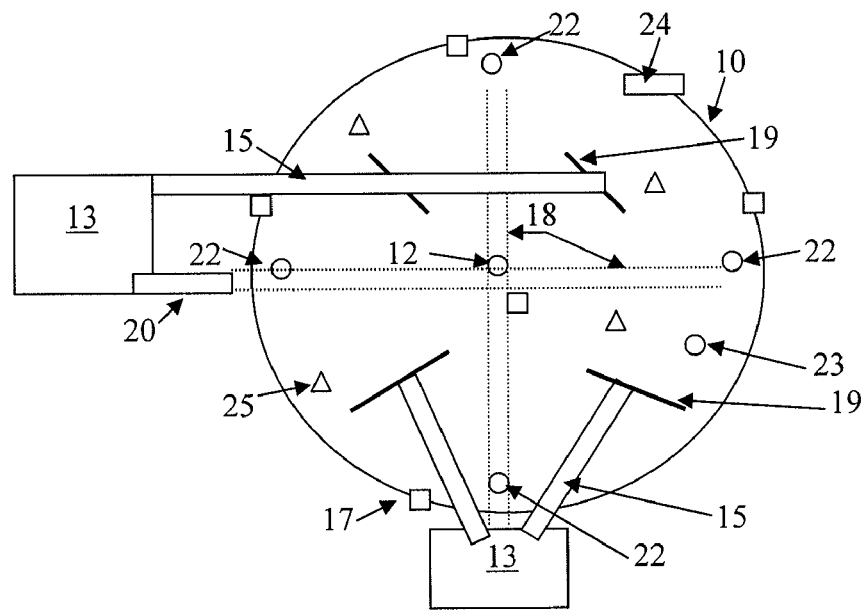
FIG. 5 is a schematic plan view of another embodiment.
Figure 6:
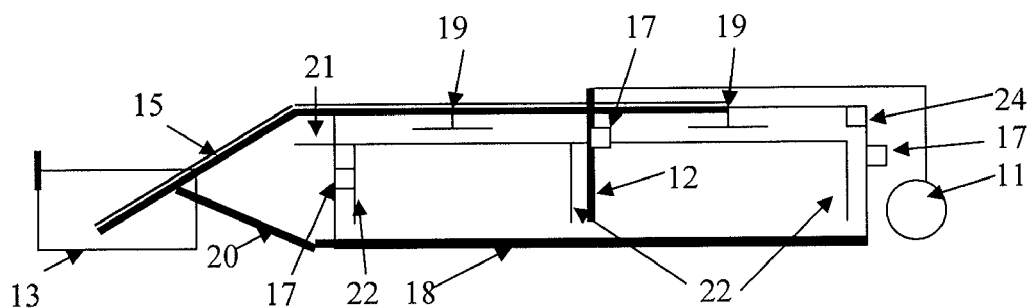
FIG. 6 is a schematic side view of the apparatus depicted in FIG. 5.

FIGS. 5 and 6 are schematic plan views of the apparatus of a very large, low profile reactor unit 10. The reactor tank can be of any size however, as illustrated, it is not as high as what is shown in FIG. 2. One or more spreaders 19, illustrated as rotary spreaders, can be used for spreading the waste evenly over the organic waste bed. The diameter of the tank 10 could be at least approximately 6 feet. In some embodiments, the diameter is approximately 40 or more feet. In some embodiments, the diameter is approximately 100 or more feet.

One or more steam injectors 12 are installed in the waste prism with the slots at the bottom half of the injector. In the illustrated embodiment, the injectors 12 are in the center several gas extractors 22 in order to pull the steam towards the gas extractors 22. In this embodiment, the gas extractors 22 are installed at the perimeter of the tank with slots at the bottom half of the extractors 22.

As discussed previously, in some embodiments, the hopper 13 can be filled with waste from the top, sealed, and purged with inert gas and/or steam and then the waste is conveyed by a conveyer system 15, such as a screw auger, to the reactor. A boiler 11 can be used to make steam. Steam can also be produced by other means, such as, for example: heat exchangers, solar collectors, geothermal, or waste heat. In some embodiments, a portion of the biogas produced by the reactor can be used to fire the boiler 11 or other steam generating apparatus.

Sensors 17 are shown installed at various locations around the tank to monitor the migration of the steam and the temperature of the waste/feedstock. A relief valve 23 may be installed to prevent over pressurizing the reactor tank. Also as discussed previously, a light and camera system 24 could be used to monitor the waste progress and shakers 25 can be used to assist settling the waste.

The above presents a description of some embodiments contemplated for carrying out the present invention. Embodiments of the invention are, however, susceptible to modifications and alternate constructions from that discussed above which are fully equivalent. Consequently, it is not the intention to limit the invention to the particular embodiments disclosed. On the contrary, the intention is to cover all modifications and alternate constructions coming within the spirit and scope of the present disclosure.

What is claimed is:

1. A method of enhancing the digestion of organic material comprising;

placing organic material into a substantially air-tight vessel;

enriching steam with a chemical configured to precipitate $H_2S$; and injecting the enriched steam into the organic material.

2. The method of claim 1, wherein the steam is enriched with ferric chloride.

3. The method of claim 1, further comprising producing the steam in a boiler.

4. The method of claim 3, wherein the steam is enriched in the boiler prior to being transported to the vessel.

5. The method of claim 1, further comprising the step of collecting biogas produced during the digestion of the organic material.

6. The method of claim 5, further comprising the step of using a portion of the biogas produced during the digestion process to fire an apparatus for producing the steam.

7. A method of producing biogas from waste material comprising:

conveying a waste material from a first container to a second substantially air-tight container;

injecting steam into the waste material in the second container;

extracting biogas from the waste material in the second container with a gas extractor;

monitoring a height level of the waste material in the second container; and controlling the amount of waste material conveyed from the first container into the second container such that as the waste material is converted into biogas, the gas extractor is maintained under the top level of waste material in the second container.

8. The method of claim 7, further comprising spreading the top level of waste material in the second container with a rotary spreader.

9. The method of claim 7, further comprising purging the first container full of waste material with inert gas or steam.

10. The method of claim 7, wherein the step of conveying comprises conveying with a screw auger.

11. The method of claim 7, further comprising conveying an indigestible material from a bottom of the second container out of the second container.

12. The method of claim 11, further comprising inoculating waste material in the first container with some of the indigestible material from the second container.

13. The method of claim 7, further comprising shaking the second container to settle and densify the waste material.

14. The method of claim 7, further comprising monitoring the temperature of the waste material in the second container.

15. The method of claim 7, wherein the step of monitoring is performed with a light and camera system.

16. The method of claim 7, further comprising adding ferric chloride to the waste material.

17. The method of claim 16, wherein the step of adding ferric chloride comprises adding ferric chloride directly into the steam.

18. The method of claim 7, further comprising removing $H_2S$ from the biogas.

* * * * *